US007223599B1

(12) United States Patent
Davidson (10) Patent No.: US 7,223,599 B1
(45) Date of Patent: May 29, 2007

(54) IMMORTALIZATION OF HUMAN POST-MITOTIC CELLS

(75) Inventor: Mercy M. Davidson, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 480 days.

(21) Appl. No.: 09/604,876

(22) Filed: Jun. 28, 2000

(51) Int. Cl.
*C12N 15/02* (2006.01)
*C12N 5/00* (2006.01)
*C12N 5/06* (2006.01)

(52) U.S. Cl. ............ 435/449; 435/346; 435/357; 435/363; 435/377; 435/325; 435/320.1; 435/455

(58) Field of Classification Search ........... 424/93.1; 435/405, 283.1, 325, 346, 347, 357, 363, 435/366, 377, 449, 455, 320.1
See application file for complete search history.

(56) References Cited

OTHER PUBLICATIONS

Watanabe et.al.; Cardiomyocyte Transplantation in a Porcine Myocardial Infarction Model, 1998, Cell Transplantation, vol. 7, No. 239-246.*
Koh et.al.; Strategies for Myocardial Repair, 1995, Journal of Interventional Cardiology, vol. 8, No. 4: 387-393.*
Wang et al (In Vitro Cellular and Developmental Biology 27(1): 63-74, Jan. 1991). See abstract.*
Makino et al (J. Clin. Invest 103(5): 697-705(1999).*
Leiden (J. Clin. Invest 103(5): 591-592(1999)).*
Connan et al (Nature (1985) 314(6008): 277-279).*
Claycomb, W., Lanson, N., Stallworth, B., Egeland, D.B., Delcaprio J.B., Bahinski, A. and Izzo, N. (1998). HL-1 cells: a cardiac muscle cell line that contracts and retains phenotypic characteristics of adult cardiomyocyte. PNAS. 95:2979-2984.
King, M., Koga, Y., Davidson, M. and Schon E. (1992). Defects in mitochondrial protein synthesis and respiratory chain activity segregate with the tRNA$^{Leu(UUR)}$ mutation associated with mitochondrial myopathy, encephalopathy, lactic acidosis and stroke like episodes. Mol. Cell. Biol. 12:480-490.
King, M. and Attardi, G. (1989). Human cells lacking mtDNA: repopulation with exogenous mitochondria by complementation. Science 246:500-503.
Singer, K., Scearce, R.M., Tuck, D.T. Whichard, L.P., Denning S.M. and Haynes B.F. (1989). Removal of fibroblasts from human epithelial cell cultures with use of a complement fixing monoclonal antibody reactive with human fibroblasts and monocytes/macrophages. J.Invest.Dermatol.92:166-170.
Bader, D., et al., "Immunochemical analysis of myosin heavy chain during avian myogenesis *in vivo* and *in vitro.*" *J. Cell. Biol.*, 95:763-770 (1982) (Exhibit 1).
Bloch, K.D., et al., "Neonatal atria and ventricles secrete atrial natriuretic factors via tissue-specific secretory pathways." *Cell*, 47:695-702 (1986) (Exhibit 2).
Brunskill, E.W., et al., "Novel cell lines promote the discovery of genes involved in early heart development." *Dev. Biol.*, 235:507-520 (2001) (Exhibit 3).
Campion, D.R., "The muscle satellite cell: a review." *Int. Rev. Cytol.*, 87:225-51 (1984) (Exhibit 4).
Cantin, M., et al., "The heart as an endocrine gland." *J. Hypertens.*, 2 (Suppl. 3):329-331 (1984) (Exhibit 5).
Chiu, R.C., et al., "Cellular cardiomyoplasty: myocardial regeneration with satellite cell implantation." *Ann. Thorac. Surg.*, 60:12-18 (1995) (Exhibit 6).
Claycomb, W.C., "Atrial-natriuretic-factor mRNA is developmentally regulated in heart ventricles and actively expressed in cultured ventricular cardiac muscle cells of rat and human." *Biochem. J.*, 255:617-620 (1988) (Exhibit 7).
Claycomb, W.C., et al., "Culture of the terminally differentiated adult cardiac muscle cell: a light and scanning electron microscope study." *Dev. Biol.*, 80:466-482 (1980) (Exhibit 8).
Constantin, B., et al., "Involvement of gap junctional communication in myogenesis." *Int. Rev. Cytol.*, 196:1-65 (2000) (Exhibit 9).
de Bold, A.J., "Atrial natriuretic factor: a hormone produced by the heart." *Science*, 230:767-770 (1985) (Exhibit 10).
Delorme, B., et al., "Expression pattern of connexin gene products at the early developmental stages of the mouse cardiovascular system." *Circ. Res.*, 81:423-437 (1997) (Exhibit 11).
Doevendans, P.A., et al., "Differentiation of cardiomyocytes in floating embryoid bodies is comparable to fetal cardiomyocytes." *J. Mol. Cell. Cardiol.*, 32:839-851 (2000) (Exhibit 12).
Eppenberger-Eberhardt, M., et al., "New occurrence of atrial natriuretic factor and storage in secretorially active granules in adult rat ventricular cardiomyocytes in long-term culture." *J. Mol. Cell. Cardiol.*, 25:753-757 (1993) (Exhibit 13).
Eppenberger-Eberhardt, M., et al., "Reexpression of α-smooth muscle actin isoform in cultured adult rat cardiomyocytes." *Dev. Biol.*, 139:269-278 (1990) (Exhibit 14).
Fabrizi, G.M., et al., "Differential expression of genes specifying two isoforms of subunits Vla of human cytochrome c oxidase." *Gene*, 119:307-312 (1992) (Exhibit 15).
Franke, W.W., et al., "Specific immunohistochemical detection of cardiace/fetal α-actin in human cardiomyocytes and regenerating skeletal muscle cells." *Differentiation*, 60:245-250 (1996) (Exhibit 16).
Fürst, D.O., et al., "Myogenesis in the mouse embryo: differential onset of expression of myogenic proteins and the involvement of titin in myofibril assembly." *J. Cell. Biol.*, 109:517-527 (1989) (Exhibit 17).
Goldman, B.I., et al., "Human fetal cardiocytes in enriched culture." *In Vitro Cell. Dev. Biol. Anim.*, 31:731-734 (1995) (Exhibit 18).
Graef, I.A., et al., "NFAT signaling in vertebrate development." *Curr. Opin. Genet. Dev.*, 11:505-512 (2001) (Exhibit 19).

(Continued)

*Primary Examiner*—Richard Schnizer
(74) *Attorney, Agent, or Firm*—John P. White, Esq.; Cooper & Dunham LLP (57) ABSTRACT

The present invention provides an immortalized human cardiomyocyte cell line. The present invention further provides a method for preparing a human immortalized cell line derived from a post-mitotic primary cell culture.

6 Claims, 5 Drawing Sheets

OTHER PUBLICATIONS

Hescheler, J., et al., "Establishment of ionic channels and signaling cascades in the embryonic stem cell-derived primitive endoderm and cardiovascular system." *Cells Tissues Organs*, 165:153-164 (1999) (Exhibit 20).

Horsley, V., et al., "NFAT: ubiquitous regulator of cell differentiation and adaptation." *J. Cell. Biol.*, 156(5):771-4 (2002) (Exhibit 21).

Jaenicke, T., et al., "The complete sequence of the human β-myosin heavy chain gene and a comparative analysis of its product." *Genomics*, 8:194-206 (1990) (Exhibit 22).

Jaffredo, T., et al., "MC29-immortalized clonal avian heart cell lines can partial differentiate *in vitro*." *Exp. Cell Res.*, 192:481-491 (1991) (Exhibit 23).

Janssen, P.M., et al., "Preservation of contractile characteristics of human myocardium in multi-day cell culture." *J. Mol. Cell. Cardiol.*, 31:1419-1427 (1999) (Exhibit 24).

Katz, E.B., et al., "Cardiomyocyte proliferation in mice expressing α-cardiac myosin heavy chain-SV40 T-antigen transgenes." *Am. J. Physiol.*, 262:H1867-H1876 (1992) (Exhibit 25).

Koga, Y., et al., "Sequence of a cDNA specifying subunit VIIc of human cytochrome c oxidase." *Nucleic Acids Res.*, 18(3):684 (1990) (Exhibit 26).

Li, R., et al., "Human pediatric and adult ventricular cardiomyocytes in culture: assessment of phenotypic changes with passaging." *Cardiovasc. Res.*, 32:362-373 (1996) (Exhibit 27).

Litzkas, P., et al., "Efficient transfer of cloned DNA into human diploid cells: protoplast fusion in suspension." *Mol. Cell. Biol.*, 4(11):2549-2552 (1984) (Exhibit 28).

Lloyd, T.R., et al., "Sympathetic innervation improves the contractile performance of neonatal cardiac ventricular myocytes in culture." *J. Mol. Cell. Cardiol.*, 22:333-342 (1990) (Exhibit 29).

Lyons, G.E., et al., "Developmental regulation of myosin gene expression in mouse cardiac muscle." *J. Cell. Biol.*, 111:2427-2436 (1990) (Exhibit 30).

Lyons, G.E., et al., "The expression of myosin genes in developing skeletal muscle in the mouse embryo." *J. Cell. Biol.*, 111:1465-1476 (1990) (Exhibit 31).

Marvin, W.J., Jr., et al., "Correlation of function and morphology of neonatal rat and embryonic chick cultured cardiac and vascular muscle cells." *Circ. Res.*, 45:528-540 (1979) (Exhibit 32).

Molkentin, J.D., "The zinc finger-containing transcription factors GATA-4, -5, and -6. Ubiquitously expressed regulators of tissue-specific gene expression." *J. Biol. Chem.*, 275:38949-52 (2000) (Exhibit 33).

Murry, C.E., et al., "Skeletal myoblast transplantation for repair of myocardial necrosis." *J. Clin. Invest.*, 98(11):2512-2523 (1996) (Exhibit 34).

Negishi, Y., et al., "Multipotency of a bone marrow stromal cell line, TBR31-2, established from ts-SV40 T antigen gene transgenic mice." *Biochem. Biophys. Res. Commun.*, 268:450-455 (2000) (Exhibit 35).

Polinger, I.S., "Separation of cell types in embryonic heart cell cultures." *Exp. Cell. Res.*, 63:78-82 (1970) (Exhibit 36).

Protas, L., et al., "L-type but not T-type calcium current changes during postnatal development in rabbit sinoatrial node." *Am. J. Physiol. Heart Circ. Physiol.*, 281:H1252-H1259 (2001) (Exhibit 37).

Quaini, F., et al., "Chimerism of the transplanted heart." *N. Engl. J. Med.*, 346:5-15 (2002) (Exhibit 38).

Salviati, L., et al., "Copper supplementation restores cytochrome c oxidase activity in cultured cells from patients with SCO2 mutations." *Biochem. J.*, 363:321-327 (2002) (Exhibit 39).

Schultheiss, T., et al., "Desmin/vimentin intermediated filaments are dispensable for many aspects of myogenesis." *J. Cell. Biol.*, 114:953-966 (1991) (Exhibit 40).

Severs; N.J., "The cardiac muscle cell." *BioEssays*, 22:188-199 (2000) (Exhibit 41).

Spurr, A.R., "A low-viscosity epoxy resin embedding medium for electron microscopy." *J. Ultrastruct. Res.*, 26:31-43 (1969) (Exhibit 42).

Steinhelper, M.E., et al., "Proliferation in vivo and in culture of differentiated adult atrial cardiomyocytes from transgenic mice." *Am. J. Physiol.*, 259 (Heart Circ. Physiol. 28):H1826-H1834 (1990) (Exhibit 43).

Van Kempen, M.J.A., et al., "Developmental changes of connexin40 and connexin43 mRNA distribution patterns in the rat heart." *Cardiovasc. Res.*, 32:886-900 (1996) (Exhibit 40); and.

Wang, D., et al., "Activation of cardiac gene expression by myocardin, a transcriptional cofactor for serum response factor." *Cell*, 105(7):851-62 (2001) (Exhibit 45).

DeCaprio, J.A., "The role of J domain of SV40 large T antigen in cellular transformation." *Biologicals*, 27:23-28 (1999) (EXHIBIT 1); and.

Fire, A., et al., "Potent and specific genetic interference by double-stranded RNA in *Caenorhabditis elegans*." *Nature*, 391:806-811 (1998) (EXHIBIT 2).

Bottenstein, J., et al., "The Growth Of Cells In Serum-Free Hormone-Supplemented Media," *Methods Enzymol.*, 58:94-109 (1979) (EXHIBIT 1).

Cozzarelli, N.R., "The Mechanism Of Action Of Inhibitors Of DNA Synthesis," *Annu. Rev. Biochem.*, 46:641-668 (1977) (EXHIBIT 3).

Hannon, G.J., "RNA Interference," *Nature*, 418:244-51 (2002) (EXHIBIT 4).

Juttermann, R., et al., Toxicity Of 5-aza-2'-deoxycytidine To Mammalian Cells In Mediated Primarily By Covalent Trapping Of DNA Methyltransferase Rather Than DNA Demethylation, *Proc. Natl. Acad. Sci. USA*, 91:11797-801 (1994) (EXHIBIT 5).

Libby, P., et al., "Long-Term Culture Of Contractile Mammalian Heart Cells In A Defined Serum-Free Medium That Limits Non-Muscle Cell Proliferation," *J. Mol. Cell Cardiol.*, 16:803-811 (1984) (EXHIBIT 7).

Mohamed, S.N., et al., "A Serum-Free, Chemically-Defined Medium For Function And Growth Of Primary Neonatal Rat Heart Cell Cultures," *In Vitro*, 19:471-478 (1983) (EXHIBIT 8).

Morkin, E., "Control Of Cardiac Myosin Heavy Chain Gene Expression," *Microsc. Res. Tech.*, 50:522-531 (2000) (EXHIBIT 9).

Nag, A.C., "Embryonic Chick Heart Muscle Cells," *Cell Culture Techniques In Heart And Vessel Research* (ed. Piper, H.M.), New York: Springer-Verlag, pp. 4-19 (1990) (EXHIBIT 10).

Nag, A.C., et al., "Factors Controlling Embryonic Heart Cell Proliferation In Serum-Free Synthetic Media," *In Vitro Cell Dev. Biol.*, 21:553-62 (1985) (EXHIBIT 11).

Weiss, A., et al., "The Mammalian Myosine Heavy Chain Gene Family," *Annu. Rev. Cell Dev. Biol.*, 12:417-39 (1996) (EXHIBIT 13).

* cited by examiner

IMMORTALIZATION OF HUMAN POST-MITOTIC CELLS

The invention was made in part with government funds under Grant Nos. HD 32062 and NS 11766 from the National Institutes of Health, U.S. Department of Health and Human Services. Therefore, the U.S. Government has certain rights in the invention.

Throughout this application, various publications are referenced by author's last name and year published and a listing of those references following the Experimental Details Section. The disclosures of these publications in their entireties are hereby incorporated by reference in order to more fully describe the state of the art as known to those skilled therein as of the date of the invention described and claimed herein.

BACKGROUND OF THE INVENTION

Cardiomyocytes have a finite life-span in culture before becoming terminally differentiated. Attempts to immortalize ventricular cardiomyocytes in order to establish a cell line that can proliferate in culture have not been successful. Recently, Claycomb et al (1998) described a mouse atrial cardiomyocyte cell line, HL-1, which can be passaged serially, differentiate, and maintain the characteristics of adult mouse cardiomyocytes. This cell line could be a useful tool for cardiovascular research, but a mouse cell line can not answer questions that are specific to the human system. Currently there is no immortalized human cardiomyocyte cell line that can proliferate and differentiate in culture and can express the adult cardiomyocyte phenotype when culture conditions are manipulated. Using an unexpected, novel and unique mitochondrial function-based method to immortalize human primary cardiomyocytes from both adult and fetal heart tissue the cell lines described in this report have been passaged for over 100 generations and can be regrown from frozen stocks. The cells express both cardiac and skeletal muscle-specific markers and can be induced to differentiate in culture to express adult skeletal muscle and cardiac muscle phenotypes.

SUMMARY OF THE INVENTION

The present invention provides an immortalized human cardiomyocyte cell line and an immortalized human vascular smooth muscle cell line. The present invention further provides a method for preparing a human immortalized cell line derived from a post-mitotic primary cell culture which comprises: (a) providing a cell culture of human primary post-mitotic cells, (b) providing a human fibroblast cell line which: (i) has been transfected with a replicable nucleic acid vector which immortalizes the fibroblast cell line, (ii) has been depleted of its mitochondrial DNA thereby rendering the fibroblast cell line subject to growth selection due incapacity to perform glycolysis; (c) co-culturing the human fibroblast cell line of step (b) with the cell culture of step (a) under appropriate conditions so that cell fusion occurs; and (d) growing the fused cells from step (c) in a selection medium which selects for cells with mitochondrial DNA, (e) selecting cells from step (d) which contain a nucleus which originated from the cells of the primary culture, so as to prepare the human immortalized cell line.

The present invention provides a human cardiomyocyte cell line designated AC10 (ATCC Patent Deposit Designation No. PTA-1501), cell line designated AC16 (ATCC Patent Deposit Designation No. PTA-1500) and cell line designated RL14 (ATCC Patent Deposit Designation No. PTA-1499) derived from nonproliferating primary culture. Additionally, the present invention provides that the cells are human cells.

DETAILED DESCRIPTION OF THE INVENTION

The present invention provides a human cardiomyocyte cell line designated AC10 (ATCC Patent Deposit Designation No. PTA-1501), cell line designated AC16 (ATCC Patent Deposit Designation No. PTA-1500) and cell line designated RL14 (ATCC Patent Deposit Designation No. PTA-1499) derived from nonproliferating primary culture. As used herein the term "nonproliferating primary cultures" encompasses cell cultures which become senescent after 2–3 passages (limited passage) and post-mitotic cells in culture. Such cultures also include those cells in culture that have exited the cell cycle and are no longer capable of undergoing mitosis (post-mitotic).

As used herein, the term "primary cultures" encompasses cells in culture that have been taken for an organism and not passaged. Primary cultures herein comprise but are not limited to cells in culture originally taken from vascular smooth muscle, skeletal myloblasts, neuronal cells, bone cells (osteoblasts, osteocytes), chondrocytes, normal cardiomyocytes.

AC10 cell line (ATCC Patent Deposit Designation No. PTA-1501), AC16 cell line (ATCC Patent Deposit Designation No. PTA-1500) and RL14 cell line (ATCC Patent Deposit Designation No. PTA-1499) were received on Mar. 16, 2000 and were accepted by the American Type Culture Collection (ATCC) 10801 University Blvd., Manassas, Va. 20110-2209, which is an International Depository Authority recognized under the provisions of the Budapest Treaty. All restrictions upon public access to these deposits will be irrevocably removed upon the grant of a patent on the subject application. The deposit will be replaced if viable samples cannot be dispensed by the ATCC.

The present invention provides an immortalized human cardiomyocyte cell line. This cell line may be derived from a post-mitotic human cardiomyocyte cell culture.

In one embodiment, the post-mitotic cell line is a cardiomyocyte cell line. In another embodiment, the post-mitotic cell line is a vascular smooth muscle cell line. In one embodiment, the post-mitotic cell line is a neuronal cell line. In one embodiment, the post-mitotic cell line is a skeletal myoblast cell line.

The present invention provides for an immortalized human cardiomyocyte cell line and an immortalized human vascular smooth muscle cell line.

In one embodiment, the cell line integrates functionally with normal or myopathic cardiac tissue as determined by measurement of syncitial beating of the tissue. This syncitial beating can be easily measured in cell culture.

The present invention provides a method for treating damaged cardiac tissue in a subject which comprises transplanting an immortalized human cardiomyocyte cell line of the present invention into a subject's heart containing damaged cardiac tissue.

The present invention provides for a method for preparing a human immortalized cell line derived from a post-mitotic primary cell culture which comprises: (a) providing a cell culture of human primary post-mitotic cells, (b) providing a human fibroblast cell line which: (i) has been transfected with a replicable nucleic acid vector which immortalizes the fibroblast cell line, (ii) has been depleted of its mitochondrial DNA thereby rendering the fibroblast cell line subject to growth selection due incapacity to perform glycolysis; (c) co-culturing the human fibroblast cell line of step (b) with the cell culture of step (a) under appropriate conditions so that cell fusion occurs; and (d) growing the fused cells from step (c) in a selection medium which selects for cells with mitochondrial DNA, (e) selecting cells from step (d) which contain a nucleus which originated from the cells of the primary culture, so as to prepare the human immortalized cell line.

In one embodiment, the cell culture of human primary non-proliferating cells in step (a) is a cell culture of primary human cardiac cells, primary human skeletal myoblast cells, human neuronal cells, or primary human osteoblast cells.

In another embodiment of the invention, the replicable vector is an SV-40 vector.

In another embodiment of the invention, the fibroblast cell line is designated DWFb1.

In another embodiment of the invention, the appropriate conditions for cell fusion in step (c) comprise incubation for about one minute in a 50% PEG solution.

The present invention provides for a method for determining whether a composition of matter inhibits cardiomyocyte cell function which comprises: (a) admixing the composition with cells of an immortalized cardiomyocyte cell line prepared by the method for preparing a human immortalized cell line of the present invention, in cell culture; and (b) determining whether the cells in step (a) exhibit normal cardiomyocyte cell function by measuring gene expression or by measuring syncitial beating in culture, wherein decreased cardiomyocyte cell function indicates that the composition inhibits cardiomyocyte cell function.

The present invention also provides for a method for determining whether a composition of matter enhances cardiomyocyte cell function which comprises: (a) admixing the composition with cells of an immortalized cardiomyocyte cell line prepared by the method of preparing an immortalized human cardiomyocyte cell line of the present invention, in cell culture; and (b) determining whether the cells in step (a) exhibit normal cardiomyocyte cell function by measuring gene expression or by measuring syncitial beating in culture, wherein increased cardiomyocyte cell function indicates that the composition enhances cardiomyocyte cell function.

In one embodiment, the composition of matter is a peptide or a peptidomimetic. In another embodiment, the composition of matter is a small organic molecule. In another embodiment, the composition of matter is a nucleic acid. In another embodiment, the composition of matter is associated with a pharmaceutically acceptable carrier.

In one embodiment, the carrier is a diluent, an aerosol, a topical carrier, an aqueous solution, an ionic solution, a nonaqueous solution or a solid support.

The selection of cells with a nucleus which originated from cells of the primary culture may be carried out in several ways. For example, one may be able to select against the growth of fibroblast cells in culture by adding to the culture antibodies specific for cell surface determinants on the fibroblasts and then adding complement to fix the cells, thereby stopping the growth of these fibroblast cells and selecting for growth of cells which have the nucleus of the cells of the primary cell cultures. Another way to so select is to screen for the expression of a gene which is specific for cells of the primary culture and which the fibroblast cells would not express. Then, one would subclone the cells which are positively expressing the specific genes and therefore would obtain a pure culture of cells which have a nucleus which originates from the primary cell culture.

In one embodiment of the invention, the cell culture of human primary non-proliferating cells of step (a) is a primary human cardiac cell culture, a primary human skeletal myoblast cell culture, a human neuronal cell culture, or a primary human osteoblast cell culture.

In another embodiment, the replicable vector is an SV-40 mammalian vector. In another embodiment of the invention, the fibroblast cell line is designated DWFb1.

In one embodiment, the pharmaceutical composition is a peptide or a peptidomimetic. In one embodiment, the pharmaceutical composition is a small organic molecule. In one embodiment, the pharmaceutical composition is a nucleic acid. In one embodiment, the pharmaceutical composition is bound to a pharmaceutically acceptable carrier. In one embodiment, the carrier is a diluent, an aerosol, a topical carrier, an aqueous solution, an ionic solution, a nonaqueous solution or a solid support.

As used herein, "mutant DNA" encompasses but is not limited to chromosomal defects (eg, trisomy 13, trisomy 18) or genetic diseases (eg, trisomy 21, Turner's syndrome [XO], Holt-Oram syndrome).

As used herein, "foreign" encompasses a DNA or RNA not in the genus of the tissue or cell.

As used herein the term "immortalize" encompasses the process of whereby a cell line can be passaged indefinitely in culture, while the cells in culture retain the functions and features of the primary cells in the culture the day the culture was begun. In one embodiment cells were immortalized by transfering the SV-40 gene into the cells of the primary culture.

As used herein, the term "primary cells" encompasses cells derived from the original tissue as obtained and manipulated to generate primary cultures.

As used herein, $\rho^0$ represents cells of the cell line rendered mtDNA-less (a cell line wherein the mitochondrial DNA of the cells is depleted).

As used herein, the "inhibitor of mitochondrial DNA replication" encompasses an agent used to deplete the mitochondrial DNA of the cells. An example of a inhibitor of mitochondrial DNA replication comprises but is not limited to Ethidium bromide.

As used herein, "post-mitotic cells" encompass cells that are no longer dividing or undergoing mitosis.

As used herein, "selecting" encompasses choosing the surviving cells in the primary culture that are composed of fused $\rho^0$ cells with nonproliferating primary cells.

As used herein, "establishing" encompasses culturing the selected cells and passing these cells a limitless number of times.

As used herein, "cloning" encompasses plating low density cells and selecting colonies that arise from a single cell.

As used herein, "screening" denotes immunocytochemical evaluation of cell specific markers.

In an embodiment of this invention the cells are cardiac cells. In another embodiment the cells have characteristic features of cardiomyocytes. In yet another embodiment the cells retain endogenous mitochondrial DNA content of the primary cells. In still another embodiment the cells are human cells.

In an embodiment the cell line expresses cardiac genes. In another the cell line expresses skeletal-muscle genes. In yet another embodiment the cell line expresses cardiac genes and skeletal-muscle genes.

In an added embodiment the primary cultures are exclusively from cardiac tissue. In another embodiment the primary cultures are from vascular smooth muscle, skeletal myocytes, neuronal cells, or cardiomyocytes from myocardial DNA mutants.

In another embodiment the primary cultures are derived from adult human tissue or from fetal human tissue.

In another embodiment the primary cultures are derived from cells that have exited the cell cycle or are post-mitotic.

The invention also provides a cell line derived from non-proliferating primary cultures.

In yet another embodiment the cells express β-myosin heavy chain and connexin-43.

Further, the present invention provides cardiomyocyte cells which when transplanted to the heart can integrate functionally forming a syncitium with normal or myopathic cardiac tissue.

The present invention provides a method for identifying a pharmaceutical preparation which is capable of enhancing or inhibiting cardiomyocyte cell growth comprising: (a) exposing the human cardiomyocyte cell line derived from nonproliferating primary cell cultures to a pharmaceutical preparation; (b) evaluating the mitochondrial function of the cell line; and (c) evaluating physiological and pathological changes of the cardiomyocyte function.

As used herein, the term "evaluating" encompasses determining the biochemical, electrophysiological or molecular genetic composition of a cell. The biochemical, electrophysiological or molecular genetics of a cell line is determined by experimental procedures described herein comprising but not limited to immunocytochemical screening, histochemistry, molecular genetic analyses and electrophysiological studies. These techniques are known by persons skilled in the art.

The invention provides a method for identifying a pharmaceutical preparation which is capable of enhancing or inhibiting cardiomyocyte cell growth comprising: (a) performing patch clamp electrophysiology on cell line derived from nonproliferating primary cell cultures; (b) exposing the cells in step (a) to a pharmaceutical composition; (c) performing patch clamp electrophysiology on the cells in step (b); and evaluating the changes in the cells from steps (a) and (c) following exposure to the pharmaceutical preparation.

In an embodiment the pharmaceutical preparation is a peptide, a peptidomimetic, a nucleic acid, a polymer, or a small molecule or an ion bound to a carrier and the carrier is a diluent, an aerosol, a topical carrier, an aqueous solution, an ionic solution, a nonaqueous solution or a solid support.

The invention provides that the cell line derived from nonproliferating primary cell cultures is used to determine differences in the normal and pathological state of cells, wherein the differences are biochemical, electrophysiological or molecular genetic.

In an embodiment the invention provides a method of identifying mitochondrial function comprising: (a) evaluating the cell line derived from nonproliferating primary cell cultures; (b) replacing the mitochondrial DNA of the cell line in step (a) with mutant DNA; (c) evaluating the cells of step (b); and (d) comparing the evaluation of step (a) to that of step (b).

In an embodiment the mutant mitochondrial DNA is maternally inherited.

The invention further provides the endogenous mitochondrial DNA can be replaced with mutant mitochondrial DNA which may be maternally inherited.

Further, the invention provides a method of identifying cardiomyopathy comprising: (a) evaluating the cell line derived from nonproliferating primary cell cultures; (b) replacing the mitochondrial DNA of the cell line in step (a) with mutant DNA; (c) evaluating the cells of step (b); and (d) comparing the evaluation of step (a) to that of step (b).

Finally, the invention provides a method of identifying nuclear mitochondrial DNA interactions comprising: (a) evaluating the cell line derived from nonproliferating primary cell cultures; (b) replacing the mitochondrial DNA of the cell line in step (a) with mutant DNA; (c) evaluating the cells of step (b); and (d) comparing the evaluation of step (a) to that of step (c).

As used herein, the term "pharmaceutical carrier" encompasses any of the standard pharmaceutical carriers such as phosphate buffered saline solution, water, emulsions such as oil/water emulsion or a triglyceride emulsion, various types of wetting agents, tablets, coated tablets and capsules. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

In the practice of any of the methods of the invention or preparation of any pharmaceutical preparation the effective amount administered will vary with the condition under investigation. For the purpose of this invention, the doses selected are known to one of skill in the art.

As used herein, characteristic features of cardiomyocytes are determined by immunocytochemical screening, histochemistry, molecular genetic analyses and electrophysiological studies.

This invention is illustrated by examples set forth in the Experimental Details section which follows. This section is provided to aid in an understanding of the invention but is not intended to, and should not be construed to, limit in any way the invention as set forth in the claims which follow thereafter.

Experimental Details

EXAMPLE 1

Human Cardiomyocyte Cell Line

Human cardiomyocyte cell lines obtained from nonproliferating primary cultures derived from both adult and fetal heart tissues using an unexpected, novel and unique method that may be applied to all primary cultures that have exited the cell cycle was established by this invention. The cell lines express both cardiac and skeletal muscle-specific genes. Presented in this invention is the only human cardiomyocyte cell line currently available. The transformed cardiomyocytes express β-myosin heavy chain and connexin-43. The presence of gap junctions and the major cardiac-specific gap junction protein, connexin-43 will allow the cells to form a syncytium and to integrate functionally with normal or myopathic cardiac tissue. Additionally, these cardiomyocyte cell lines are useful tools for evaluating pharmacological, electrophysiological, and biochemical effects of pharmaceutical preparations. These cell lines are potentially invaluable in vitro models to study differentiation of muscle in normal and pathological states with wide applicability in cardiovascular and neuromuscular research. In addition, by methods described previously (King, et al.), it is possible to deplete the cardiomyocyte cell lines of their endogenous mtDNA content and repopulate them with mtDNA containing mutations commonly associated with maternally inherited cardiomyopathies thus providing an excellent in vitro model to study the tissue specific phenotype that may segregate with the respective mutation.

Materials and Methods

Primary Cultures

Adult ventricular heart tissue was obtained from the heart transplantation facility and fetal heart was obtained from the Department of Obstetrics and Gynecology, Columbia University, (IRB#0534)(ventricular heart tissue is illustrative as described herein, subsequent experiments used the same method with different tissue). In later experiments human tissue was obtained from the same facility and used to establish primary cell cultures of vascular smooth muscle, skeletal myloblasts, neuronal cells or cardiomyocytes with normal or pathological myocardial DNA (mutants.) The ventricular tissue was dissected and minced under a dissection microscope. The tissue was transferred to a glass chamber and extensively trypsinized at 37° C. The enzymatically dissociated cells consisting of a mixture of all the constituent cell types of cardiac tissue were resuspended in DMEM F-12, supplemented with 12.5% Fetal Bovine Serum (FBS) and penicillin-streptomycin and were allowed to attach for an hour. The medium containing a higher concentration of cardiomyocytes that did not attach was transferred to a fresh 10 cm$^2$ dish and cultured at 37° C. in 5% $CO_2$.

The culture dishes had fibroblasts which were co-cultured with the cardiomyocytes. These fibroblasts were removed by repeated selective plating and by repeated complement fixation using an antibody, 1B10, (Sigma Chemical Co.) to the surface protein of fibroblasts (Singer et al, 1989). This resulted in cultures with a very high percentage of cardiomyocytes. As expected, the primary cardiomyocytes obtained from fetal tissue underwent several more population doublings than those derived from adult heart tissue.

SV-40 Transformations (Transforming a Normal Fibroblast Cell Line)

Since the primary cultures stopped dividing, an indirect method was used to transfer the SV-40 gene in order to immortalize the cardiomyocytes. Used was a fibroblast cell line (DWFb1) transfected with a plasmid pNRS1, an SV-40 based mammalian vector, and depleted of its mitochondrial DNA (mtDNA) by treatment with ethidium bromide. DWFb1 was entirely dependent on glycolysis for energy requirements and was auxotrophic to uridine and pyruvate. A few days after the final complement fixation step, DWFb1 cells were layered on the cardiomyocytes and allowed to attach for 4 hours at 37° C. (fusing the ρ$^0$ cells with primary cells in culture). The cells were fused with a 50% polyethylene glycol (PEG) solution for one minute, excess PEG was removed, the cells were gently rinsed in 10% dimethyl sulfoxide (DMSO) in culture medium, and subsequently grown under selection in uridine-free Dulbecco's Modified Eagle's Medium (DMEM) F-12 medium supplemented with 12.5% dialysed Fetal Bovine serum (FBS). This selection will eliminate the mtDNA-less cells (ρ$^0$) cells that have not fused with the cardiomyocytes (selecting cells for a cell line).

Figure 1:
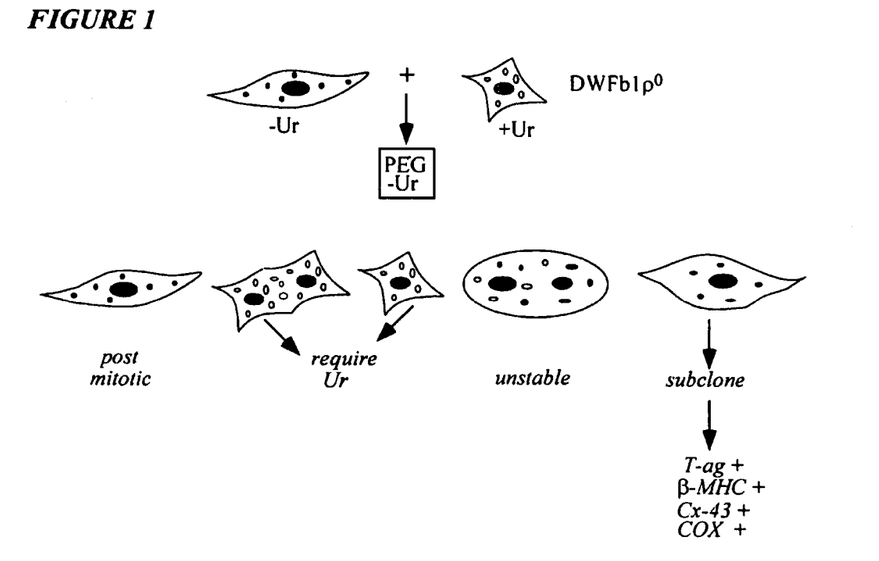
FIG. 1: Schematic diagram to illustrate generation of immortalized human cardiomyocyte cell lines.

Selection—The surviving hybrid cells were plated at low density and subcloned with glass cloning rings (establishing a clone/colony). About 40–50 colonies, each grown from a single cell, were picked from both adult, and fetal cardiomyocyte fusions. The clones were grown under selection, and screened for specific cell-type markers by immunocytochemical and molecular genetic analyses. FIG. 1 describes schematically, the method used to generate our cardiomyocyte cell lines.

Immunocytochemical Screening

Cells from the clones plated on glass coverslips were fixed with 4% paraformaldehyde in phosphate buffered saline (PBS) for 1 hour, incubated with monoclonal antibody to SV-40 large T-antigen for 1 hour, and visualized by Texas Red conjugated secondary antibody. Clones that were positive for the large T-antigen were selected and screened immunocytochemically for the expression of muscle cell lineage markers, such as β-myosin heavy chain, connexin-43, vimentin and desmin. The cells were incubated with the primary antibody for an hour at room temperature, and visualized with the appropriate secondary antibody conjugated with either FITC or Texas red. The cells were examined with a Zeiss fluorescent microscope using epi-illumination as described and the images captured using SCION 1.60 image analysis software.

Histochemistry

In order to evaluate mitochondrial function, succinic dehydrogenase (SDH) and cytochrome c oxidase (COX) histochemistry was performed. Cells plated on glass coverslips were air dried and incubated with the respective substrates, mounted on glass slides and studied with a Zeiss microscope, (King et al, 1992)

Molecular Genetic Analyses

Total RNA was extracted from the clones using 'Totally RNA', an RNA isolation kit from Ambion. Reverse transcriptase PCR (RT-PCR) was performed using mRNA isolated from the clones with the following primers. The forward primer was located at nt 5735–5755 in exon 3 and the backward primer was located at nt 6333–6313 in exon 4. This primer set will amplify a 599 base pair fragment from the β-myosin heavy chain gene. RT-PCR was performed concurrently with the same samples using primers located within the cardiac muscle specific subunit of the cytochrome c oxidase gene (COX VIIc) as a control. The forward primer was located at nucleotide 1–24 (gcagagcttccagcggctat), and the backward primer was located at nucleotide 292–317 (catatgccatactagatatgtttgtc). The expected size of the amplified fragment is 300 bp.

Electrophysiological Studies

The cardiomyocyte cell lines were grown on glass coverslips. Current recordings were performed by whole cell patch clamp electrophysiology. Under standard recording conditions, the resting membrane potential was recorded in all the selected cardiomyocyte clones. Dye coupling was performed by microinjection of Lucifer yellow into cells using a micromanipulator. The intracellular infusion of Lucifer yellow into the surrounding cells was observed and recorded.

Results

Generation of immortalized cardiomyocyte cell lines.

Primary cardiomyocyte cultures from adult and fetal heart were repeatedly and selectively plated and complement fixed. This method eliminated most of the other cell types in the primary cultures and enriched for the cardiomyocyte content. By fusion with a $\rho^0$ fibroblast cell line carrying the SV-40 gene and with selection that will permit the growth of only those cells that were fused, several growing colonies were observed. The parental DWFb1 cells were eliminated in the uridine-free medium, because they are respiration-incompetent. The unfused cardiomyocytes were terminally differentiated and did not survive passaging. Therefore, the surviving cells are fusion products of the cardiomyocytes and DWFb1, which were subsequently subcloned and more than 50 clones were isolated and cultured. The cells were passaged continuously in medium enriched with mitogens and growth factors for over 80 passages. At every stage of culture, several vials of cells were frozen in order to maintain stocks. These frozen stocks were found to be viable when thawed for regrowth.

Characterization of Cardiomyocyte Cells

Immunocytochemical Screening

Figure 2A:
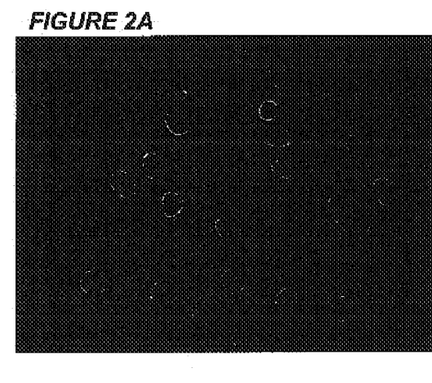
FIGS. 2A–2D: Immunocytochemical staining of cardiomyocyte cell line AC16 with monoclonal antibodies to SV-40 large T-antigen (FIG. 2A); β-myosin heavy chain (FIG. 2B); desmin (FIG. 2C), and connexin-43 (FIG. 2D).
Figure 2B:
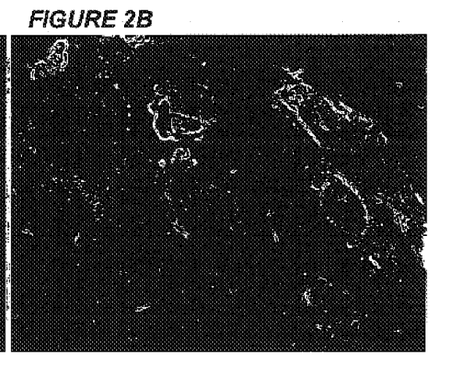
Figure 3:
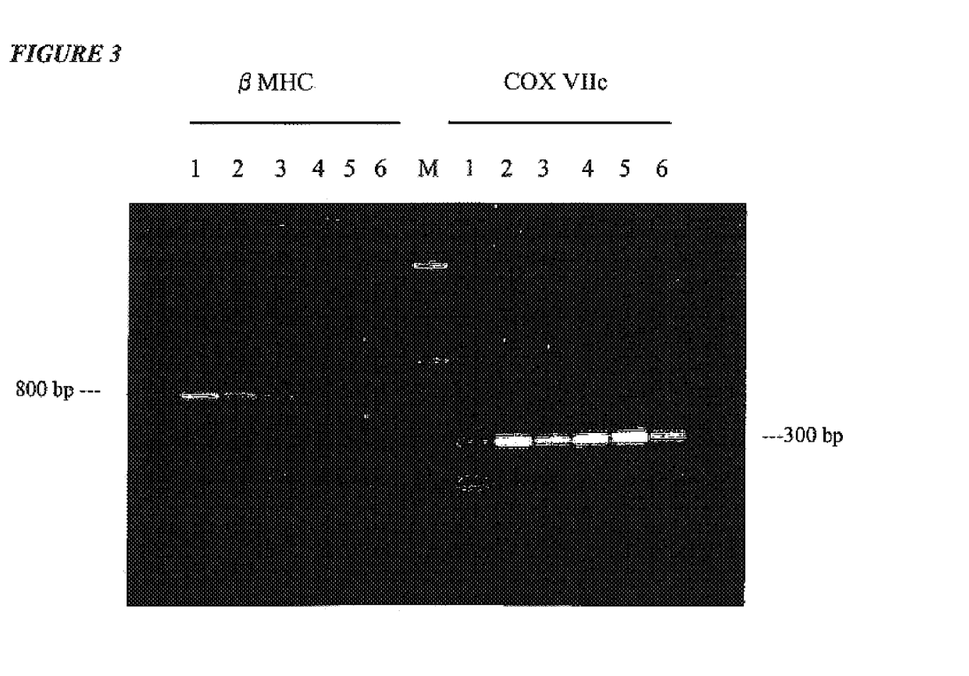
FIG. 3: RT-PCR of cardiomyocyte clones (CM) showing, β-myosin heavy chain mRNA, and COX subunit VIIc mRNA. Lane 1 adult human heart, 2–5 CM clones, 6 human fibroblasts. M=DNA size marker.

All 50 clones tested were positive for the large T-antigen by immunocytochemistry indicating that they were immortalized by the SV-40 gene carried by the DWFb1 cells (FIG. 2a). Six out of fifty adult cardiomyocyte clones and 14 out of fifty fetal cardiomyocyte clones expressed β-myosin heavy chain by immunostaining (FIG. 2b), and by RT-PCR, (FIG. 3). Five representative clones that co-expressed the large T-antigen and β-myosin heavy chain (AC1, AC10, AC12, AC16 and RL14) were selected for further analysis.

Figure 2C:
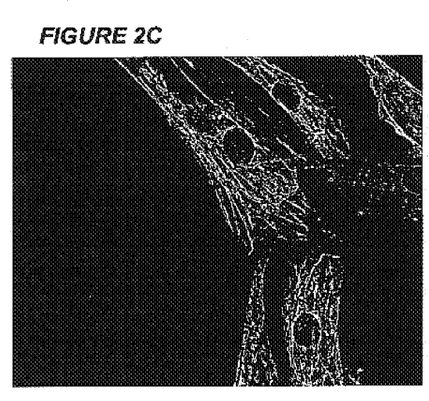
Figure 2D:
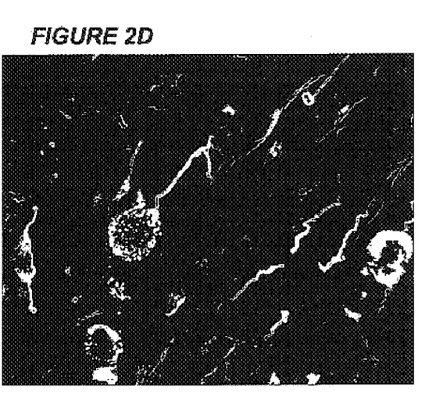

The clones exhibited the same growth properties and tissue-specific markers, irrespective of whether they originated from the adult or the fetal tissue. The cells expressed connexin-43, a cardiac tissue specific gap junction protein (FIG. 2d). The cells did not stain with vimentin, data not shown), which is normally expressed by fibroblasts. However, they expressed desmin (FIG. 2c), which is a muscle-specific marker, expressed by both skeletal and cardiac muscle.

Molecular Genetic Analyses

RT-PCR demonstrated the presence of β-myosin heavy chain mRNA which is specifically expressed by cardiomyocytes. COX VIIc which is a muscle-specific subunit of cytochrome c oxidase present in heart and skeletal muscle was also present in the cardiomyocytes (FIG. 3).

Electrophysiological Studies:

The cardiomyocyte-derived cell lines were examined briefly using patch clamp electrophysiology. Under standard recording conditions, the undifferentiated cardiomyocyte-derived cells were found to have stable, but low (−30 to −45 mV), resting membrane potentials. Consistent with their undifferentiated state, the cells lacked obvious voltage-activated conductances in whole-cell voltage-clamp recordings.

Intracellular infusion of Lucifer yellow revealed dye coupling of 3–6 cells per recorded cell, consistent with the presence of gap junction coupling between the cells. Presence of the gap junction protein connexin 43 was confirmed by immunocytochemistry.

Discussion

Cardiomyocyte cell lines (AC1, AC10, AC12, AC16 and RL14) have been established from non-proliferating primary cultures derived from both adult and fetal heart tissues, vascular smooth muscle cells, skeletal myoblasts, neuronal cells or cardiomyocytes from myocardial DNA mutants by an unexpected novel and unique method that may be used with all primary cultures that have exited the cell cycle. Transfection of cells with vectors containing foreign DNA has been accomplished with cells.

This novel technique utilizes a mitochondrial function-based method to indirectly introduce the SV-40 gene into cells which are normally intractable to standard transformation techniques (FIG. 1). First a normal fibroblast cell line was transformed with an SV-40 based mammalian vector to immortalize it. This cell line expresses the large T-antigen by immunocytochemistry. Subsequently, this cell line was treated with ethidium bromide to render it mtDNA-less, $\rho^0$, (King et al). The transformed $\rho^0$ fibroblasts, ($\rho^0$ DWFb1) are auxotrophic for uridine and pyruvate. They will grow only in medium supplemented with uridine and pyruvate since they are totally glycolytic and do not have a functional respiratory chain. By fusing postmitotic primary cells with $\rho^0$ DWFb1 and by using a uridine-free selection that permits the growth of only those cells which have re-entered the cell cycle with normal respiratory chain function, immortalized human cardiomyocyte cell lines which still retain their endogenous mitochondrial DNA content are established herein. By employing suitable selection and subsequent subcloning steps followed by screening for cell lineage markers, clones were picked that express characteristics of adult human cardiomyocytes. By this protocol it may be possible to identify and characterize other clones based on the expression of specific markers of the different cell types that are present in the primary cultures and under the control of the nuclear genome.

The parental fibroblasts used for fusion (DWFb1) lack a functional respiratory chain, and therefore depend on glycolysis and uridine for their growth and survival. They are negative when stained for cytochrome c oxidase activity (COX). After fusion with cardiomyocytes, they have a fully functional respiratory chain activity as shown by the presence of normal cytochrome c oxidase (COX) activity, indicating the cardiomyocyte origin of mtDNA. The cell lines developed by this unique method have retained both the nuclear, and the mtDNA, from the cardiomyocytes. The fibroblast line were used as a vehicle to transfer the SV-40 gene to immortalize the primary heart cells, when all other methods for transformation failed.

Efforts were focused to obtain cardiomyocyte-enriched primary cultures, by selective removal of fibroblasts. Therefore, our chances of generating relatively pure populations of transformed cardiomyocytes was high. As shown schematically in FIG. 1, our fusion and selection method favors the growth of only those cardiomyocytes that have fused with $\rho^0$ DWFb1 and contain the SV-40 gene. The unfused DWFb1 cells and the primary cardiomyocytes will not divide and grow under these culture conditions. The multinucleated cells were unstable and eliminated during subsequent passages.

Fifty large T-antigen positive subclones were selected and further screened immunocytochemically to characterize their tissue specific phenotype. Demonstrated in both the AC and RL clones was the presence of the β-myosin heavy chain and its mRNA as confirmed by RT-PCR. β-myosin heavy chain is expressed specifically by adult cardiomyocytes. All the cell lines expressed connexin-43, a major cardiomyocyte specific gap junction protein. Lucifer yellow, when microinjected into the cell, spread to the surrounding cells indicating that the gap junctions are open and the cells can communicate with each other. The cultures did not stain with antibody to vimentin, indicating that the cells are not controlled by the fibroblast nucleus. On the other hand, based on the staining with antibodies to desmin, β-myosin heavy chain, and connexin-43, the clones seem to be driven by the cardiomyocyte nucleus and express features characteristic of both cardiac and skeletal muscle. There is no evidence of any skeletal muscle in the tissue samples that were used to generate cell lines with both cardiac and skeletal muscle phenotypes. The skeletal muscle markers are perhaps expressed as a consequence of the transformation of the primary cardiomyocytes by the SV-40 gene resulting in their de-differentiation. Using the same reasoning, it may therefore be possible to induce these cardiomyocytes to differentiate in culture either towards the cardiac muscle or to the skeletal muscle lineage. These studies are currently being performed in the laboratory and may be a useful model in the study of both cardiac and skeletal muscle.

The cells exhibit a low resting membrane potential consistent with their undifferentiated state. Studies are currently being undertaken to determine if changes in their state of differentiation can result in changes in their electrophysiological characteristics.

Since heart cells are terminally differentiated they cannot respond to injury to heart muscle as occurs during heart attacks. The human cardiomyocyte cell lines described here may be useful for transplantation on damaged myocardium to repair and restore normal function. The potential use of these cells in cell transplantation techniques is important due to the presence of gap junctions and the cardiac muscle-specific gap junction protein, which play a role in cell communication. These cells when transplanted on heart tissue may potentially fuse with native myocardium, form a syncytium and functionally integrate.

Secondly, the cell lines provide a tissue culture model to evaluate pharmacological and physiological effects of drugs in order to devise and test therapeutic strategies. Cells generated by this method are evaluated as previously described by patch clamp electrophysiology, biochemical tests (eg. histochemistry) or molecular genetic analysis. The cells are then exposed by methods known to those skilled in the art, to a pharmaceutical preparation. After exposure the cells are again evaluated by the previously described methods. A comparison of the cells before exposure to the pharmaceutical preparation and after is indicative of the effectiveness of the preparation in enhancing or inhibiting cell growth. This may be a useful model in studying biochemical and molecualr genetic changes in cardiovascular disease as a result of the treatment with a pharmaceutical preparation.

Several point mutations of the mtDNA are associated with maternally inherited cardiomyopathy as the predominant or exclusive clinical feature. Using techniques developed and described herein, it is possible to deplete the cardiomyocyte cell lines of their endogenous mtDNA content and repopulate them with mtDNA harboring pathogenic mutations to evaluate the pathogenesis of maternally inherited cardiomyopathies, mitochondrial function or differences in the normal and pathological state of cells. This may reveal if there is a cardiac tissue specific phenotype that segregates with the cardiomyopathy specific mutations.

This method of immortalization of post mitotic cells that have a finite lifespan in culture has a wide applicability to practically all cell types. This technology has been successfully utilized to generate not only human ventricular cardiomyocyte cell line but also vascular smooth muscle (VSM) cell line from human aorta and human skeletal myoblasts from muscle biopsies. Prior to this invention the primary VSM cells were unable to grow and divide beyond 14 passages, when they became senescent. After immortalization using the method disclosed in this invention cells have been successfully passaged over 50 generations and still continue to divide and grow. The skeletal myoblasts have also been passaged for 25 generations. Neuronal cells have also been successfully immortalized using this technique and are being characterized.

In summary, this invention developed human ventricular cardiomyocyte cell lines which can proliferate in culture through several passages, and can be repeatedly frozen, thawed, and propagated. The cells express both cardiac muscle and skeletal muscle-specific markers. When cultured under suitable conditions, these pluripotent cells may be allowed to differentiate into either the cardiac muscle or the skeletal muscle lineage. They are potentially invaluable in vitro models to study differentiation of muscle in normal and pathological states with wide applicability to cardiovascular and neuromuscular research. This invention presents the first available human cardiomyocyte cell line of its kind. In general the methods taught in this invention can be applied to any primary cell culture that is post mitotic.

EXAMPLE 2

Vascular Smooth Cells

Human vascular smooth cells (VSM), from human aorta were immortalized by the same technique that was used for generating the proliferating cardiomyocyte cell lines. The VSM cells have a finite lifespan up to about 12 population doublings. These cells at passage 9 were fused with a mitochondrial DNA-less (rho zero), fibroblast cell line, ($\rho^0$ DWFb1) that carried the SV-40 gene, and was dependent on uridine for growth. Several clones were selected in medium containing no uridine. This medium permitted the growth of only the VSM cells that fused with the $\rho^0$ DWFb1 cells. The parental DWFb1 cells were eliminated in selection. The unfused VSM cells eventually with advanced passaging were also eliminated.

Figure 4A:
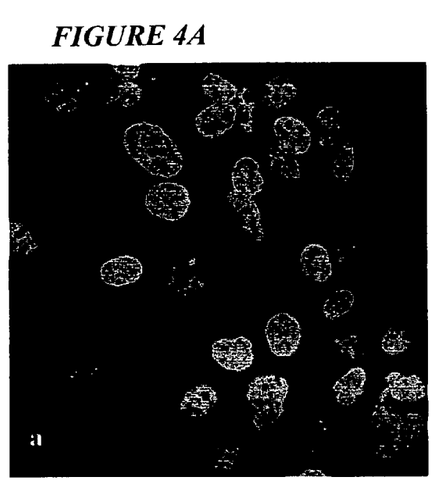
FIGS. 4A–4B: Vascular smooth cells stained with monoclonal antibodies to SV-40 large T-antigen (FIG. 4A) and succinate dehydrogenase (SDH) histochemistry (FIG. 4B).
Figure 4B:
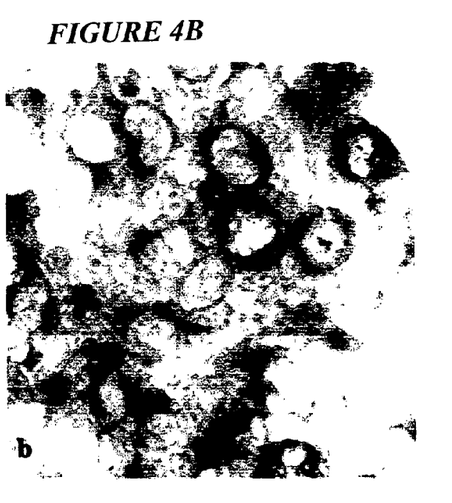

These immortalized VSM cells express the large T-antigen, FIG. 4A, and have been passaged over 50 times. On screening for mitochondrial function, they exhibit normal succinate dehydrogenase activity, FIG. 4B, indicative of the VSM-origin of the mitochondria. The parental DWFb1 cells were rho zero. We have done limited characterization of these transformed VSM cells. Further studies are necessary and are currently being performed in our laboratory.

REFERENCES

Claycomb W, Lanson N, Stallworth B, Egeland D B, Delcaprio J B, Bahinski A, and Izzo N (1998) HL-1 cells: a cardiac muscle cell line that contracts and retains phenotypic characteristics of adult cardiomyocyte. PNAS. 95:2979–2984

King M, Koga Y, Davidson M, and Schon E (1992) Defects in mitochondrial protein synthesis and respiratory chain activity segregate with the tRNA$^{Leu(UUR)}$ nutation associated with mitochondrial myopathy, encephalopathy, lactic acidosis, and stroke like episodes. Mol Cell Biol. 12:480–490

King M, and Attardi G (1989) Human cells lacking mtDNA: repopulation with exogenous mitochondria by complementation. Science. 246:500–503

Singer K, Scearce R M, Tuck D T, Whichard L P, Denning S M, and Haynes B F (1989). Removal of fibroblasts from human epithelial cell cultures with use of a complement fixing monoclonal antibody reactive with human fibroblasts and monocytes/macrophages. J. Invest. Dermatol. 92:166–170.

What is claimed is:

1. An immortalized human undifferentiated cardiomyocyte cell line, wherein the cardiomyocyte cell line is designated AC16 (ATCC Designation No. PTA-1500).

2. An immortalized human undifferentiated cardiomyocyte cell line, wherein the cardiomyocyte cell line is designated AC10 (ATCC Designation No. PTA-1501).

3. An immortalized human undifferentiated cardiomyocyte cell line, wherein the cardiomyocyte cell line is designated RL14 (ATCC Designation No. PTA-1499).

4. A method for preparing a human undifferentiated immortalized cell line derived from a post-mitotic primary cell culture which comprises:
   (a) providing a cell culture of human primary post-mitotic cells;
   (b) providing a human fibroblast cell line which
      (i) has been transfected with a replicable nucleic acid vector expressing SV40 large T antigen which immortalizes the fibroblast cell line, and
      (ii) has been depleted of its mitochondrial DNA;
   (c) co-culturing the human fibroblast cell line of step (b) with the cell culture of step (a) under appropriate conditions so that cell fusion occurs;
   (d) growing the fused cells from step (c) in a selection medium which selects for cells with mitochondrial DNA; and
   (e) selecting cells from step (d) which
      (i) contain a replicable vector that expresses SV-40 large T antigen, and
      (ii) express one or more genes specifically expressed by the primary post-mitotic cell of step (a),
   so as to prepare the human immortalized cell line.

5. The method of claim 4, wherein the cell culture of human primary non-proliferating cells in step (a) is a cell culture of primary human cardiac cells, primary human skeletal myoblast cells, human neuronal cells, or primary human osteoblast cells.

6. The method of claim 4, wherein the appropriate conditions for cell fusion in step (c) comprise incubation for about one minute in a 50% PEG solution.

* * * * *

UNITED STATES PATENT AND TRADEMARK OFFICE
CERTIFICATE OF CORRECTION

| | | |
|---|---|---|
| PATENT NO. | : 7,223,599 B1 | Page 1 of 1 |
| APPLICATION NO. | : 09/604876 | |
| DATED | : May 29, 2007 | |
| INVENTOR(S) | : Mercy M. Davidson | |

It is certified that error appears in the above-identified patent and that said Letters Patent is hereby corrected as shown below:

In the specification at column 1, lines 4-8:

"The invention was made in part with government funds under Grant Nos. HD 32062 and NS 11766 from the National Institutes of Health, U.S. Department of Health and Human Services. Therefore, the U.S. Government has certain rights in the invention." should read -- This invention was made with government support under grant numbers HD032062 and NS11766 awarded by the National Institutes of Health, U.S. Department of Health and Human Services. The U.S. government has certain rights in the invention. --

Signed and Sealed this
First Day of March, 2016

Michelle K. Lee
*Director of the United States Patent and Trademark Office*